United States Patent [19]

Hagedorn et al.

[11] Patent Number: 5,670,694

[45] Date of Patent: Sep. 23, 1997

[54] PROCESS FOR THE PREPARATION OF 2,4-DICHLORO-5-FLUOROBENZONITRILE AND 2,6-DICHLORO-3-FLUOROBENZONITRILE

[75] Inventors: Ferdinand Hagedorn; Helmut Fiege, both of Leverkusen; Reinhard Lantzsch, Wuppertal, all of Germany

[73] Assignee: Bayer Aktiengesellschaft, Leverkusen, Germany

[21] Appl. No.: 610,772

[22] Filed: Mar. 4, 1996

[30]  Foreign Application Priority Data

Mar. 7, 1995 [DE] Germany .............. 195 07 912.4

[51] Int. Cl.$^6$ .................................. C07C 253/24
[52] U.S. Cl. ...................................... 558/327
[58] Field of Search ................................ 558/327

[56]  References Cited

U.S. PATENT DOCUMENTS

| | | |
|---|---|---|
| 4,582,647 | 4/1986 | Bayerl et al. . |
| 5,187,295 | 2/1993 | Schach . |
| 5,464,810 | 11/1995 | Haas et al. . |
| 5,475,164 | 12/1995 | Bussmann . |

FOREIGN PATENT DOCUMENTS

| | | |
|---|---|---|
| 0158928 | 10/1985 | European Pat. Off. . |
| 0431373 | 6/1991 | European Pat. Off. . |
| 0433124 | 6/1991 | European Pat. Off. . |
| 0500083 | 8/1992 | European Pat. Off. . |
| 0609734 | 8/1994 | European Pat. Off. . |
| 1189976 | 5/1963 | Germany . |
| 4340854 | 9/1995 | Germany . |

OTHER PUBLICATIONS

Chemical Abstracts, vol. 113, abstract No. 113:77918q, abstract of CN 1,031,074, p. 738, (1990).
I. Shigehara, CA115:182866, Preparation of 2,6–dichloro–3–fluorobenzonitrile, (1991).

*Primary Examiner*—Johann Richter
*Assistant Examiner*—John Peabody
*Attorney, Agent, or Firm*—Sprung Horn Kramer & Woods

[57]  ABSTRACT

A mixture of 2,4-dichloro-5-fluorotoluene and 2,6-dichloro-3-fluorotoluene which cannot be separated in an economically efficient manner and can be reacted individually to give the corresponding benzonitriles is subjected according to the invention to ammoxidation in the form of this mixture and then separated at the stage of the benzonitriles by methods known to the person skilled in the art.

8 Claims, No Drawings

PROCESS FOR THE PREPARATION OF 2,4-DICHLORO-5-FLUOROBENZONITRILE AND 2,6-DICHLORO-3-FLUOROBENZONITRILE

The present invention relates to a process for the preparation of 2,4-dichloro-5-fluorobenzonitrile and 2,6-dichloro-3-fluorobenzonitrile, in which a mixture of 2,4-dichloro-5-fluorotoluene and 2,6-dichloro-3-fluorotoluene is converted by joint ammoxidation into the mixture of the nitriles mentioned and this is then separated into the pure nitriles by methods known to the person skilled in the art.

The nitriles mentioned are useful intermediates for pharmaceuticals and plant protection agents (EP 609 734).

Various synthetic routes have already been described for the preparation of 2,4-dichloro-5-fluorobenzonitrile. The reaction of 2,4-dichloro-5-fluorobenzoic acid with thionyl chloride in the presence of catalytic amounts of dimethylformamide has thus been disclosed; the further reaction of the obtained acid chloride with ammonia to give the corresponding acid amide and its dehydration with phosphorus oxychloride then yields the associated benzonitrile (EP 433 124). Furthermore, the bromination of 1,3-dichloro-4-fluorobenzene to give 1-bromo-2,4-dichloro-5-fluorobenzene and its further reaction with copper(I) cyanide to give the desired nitrile is known (EP 500 083). A further synthetic route in which 2,4-dichloro-5-fluoronitrobenzene is reduced to the amino compound and this is reacted, after diazotization and Sandmeyer reaction, with cyanide to give the nitrile is described in CN 1,031,074 (cited by C. A. 113 (1990), 77918q). Finally, EP 431 373 describes a synthesis in which 2,4-dichloro-fluorobenzene is trichloromethylated using carbon tetrachloride and the substituted benzotrichloride thus obtained is reacted with aqueous ammonia to give the nitrile.

All the above synthetic methods are affected by disadvantages, which are serious in some cases, with, for example, expensive starting materials, the handling of bromine, copper cyanide or carbon tetrachloride or a large number of reaction steps or working in dilute solutions making access to the desired nitrile difficult, or making the particular preparation process uneconomic.

For 2,6-dichloro-3-fluorobenzonitrile, previously only a very complicated synthesis process has been described in which 3-chloro-2,4-difluoro-nitrobenzene is reacted by replacement of the fluorine atom in position 2 with cyanide in dimethylformamide as a reaction medium to give 2-chloro-3-fluoro-6-nitro-benzonitrile and converted by chlorolysis of the nitro group at 190° C. into the desired nitrile. In particular, the last of the reaction steps mentioned is to be regarded as not very promising industrially because of the high material pollution of the equipment used (JP 03/90057 (1991); cited by C. A. 115 (1991), 182866k).

It was therefore the object of the present invention to provide a simple, industrially and economically advantageous preparation process for the two isomeric nitriles.

An isomer mixture of 2,4-dichloro-5-fluorotoluene and 2,6-dichloro-3-fluorotoluene which can be prepared easily according to German Offenlegungsschrift 4 340 854 by double nuclear chlorination of m-fluorotoluene is virtually impossible to separate by fractional distillation because of the too low boiling point difference. It has now been found that a mixture of the desired dichloro-fluorobenzonitriles is obtained by ammoxidation of the dichloro-fluorotoluene mixture mentioned and that this mixture of the nitriles can be separated by methods known to the person skilled in the art and thus the desired nitriles can be individually isolated.

The invention relates to a process for the preparation of 2,4-dichloro-5-fluorobenzonitrile and 2,6-dichloro-3-fluorobenzonitrile, which is characterized in that a mixture of 2,4-dichloro-5-fluorotoluene and 2,6-dichloro-3-fluorotoluene is reacted with ammonia, air and steam in a molar ratio of dichloro-fluorotoluene:ammonia:air:steam of 1:1–3:7.5–15:0–10 in the gas phase at a temperature of 350° to 550° C. on an ammoxidation catalyst to give a mixture of the nitriles mentioned and this is then separated by methods known to the person skilled in the art.

The mixture of the dichloro-fluorotoluenes mentioned can be employed according to the invention for ammoxidation in any desired isomer ratios. Preferably, mixtures having a content of 60 to 90% of 2,4-dichloro-5-fluorotoluene and 40 to 10% of 2,6-dichloro-3-fluorotoluene are employed.

In a furthermore preferred manner, the ammoxidation is carried out in the presence of steam; the molar ratio of the starting substances is then dichloro-fluorotoluene:ammonia:air:steam=1:1.1–1.5:7.5–15:5–10.

The catalysts which can be employed for the ammoxidation are known to the person skilled in the art. For this purpose, for example, compounds of molybdenum, bismuth, vanadium or chromium, if appropriate with further additives, on activated acidic carrier substances, for example boron phosphorus oxide and/or tin phosphate and/or silicic acid and/or alumina, can be employed (German Patent Specification 1 189 976; German Patent Specification 1 770 841). Further suitable catalysts contain vanadium phosphate (dissertation F. G. Martin, Erlangen 1989; DD 256 129). These and similar ammoxidation catalysts have already been employed, for example, for the reaction of other nuclear-halogenated toluenes, such as chlorotoluenes and dichlorotoluenes.

The temperature for the ammoxidation is in the range from 350° to 550° C., preferably from 400° to 530° C. It is dependent, inter alia, on the nature of the catalyst selected: for example, contact catalysts activated with MoBi thus tend to require a somewhat higher temperature in the range mentioned, while V-containing catalysts are already efficient in the lower part of the temperature range mentioned.

The product mixture formed during the ammoxidation is composed essentially of the two nitriles, the incompletely reacted dichloro-fluorotoluenes and water of reaction. To these are added unused ammonia and unused oxygen. The useful organic substances, namely the dichloro-fluorobenzonitriles and the dichloro-fluorotoluenes, can easily be separated from any possible impurities by steam distillation and, after removing the water, subjected to precision distillation. In this process, the content of dichloro-fluorotoluenes is first distilled off and can be fed back into the reaction.

The further separation of the remaining two nitriles is carried out by methods known to the person skilled in the art, such as by fractional distillation, solution crystallization or melt crystallization as well as preparative chromatography. Preferably, fractional distillation or crystallization is employed as such a separation method. In the case of the use of fractional distillation, this is preferably carried out in vacuo. For example, under a pressure of 140 mbar 2,4-dichloro-5-fluorobenzonitrile is thus obtained at a boiling point of 170.3° C., while 2,6-dichloro-3-fluorobenzonitrile boils at 182.2° C. under the same pressure. In this manner, both nitriles can be isolated with a purity of more than 99%. It is equally possible to treat the mixture obtained from the ammoxidation with seed crystals of one of the desired dichloro-flurobenzonitriles without removal of the unreacted dichloro-fluorotoluenes and to recover the crystallisate obtainable in this way of the dichloro-fluorobenzonitrile concerned by filtration; preferably seeding is carried out to obtain 2,4-dichloro-5-fluorobenzonitrile.

EXAMPLE 1

A gas mixture generated from dichloro-fluorotoluene, ammonia, air and water in the molar ratio of about 1:3:13.5:10 was passed at temperatures between 500° and 530° C. over 170 ml of catalyst granules having a grain diameter of 0.25 mm, consisting of boron phosphorus oxide/ tin phosphate/silicic acid carrier material activated with 3.5% of molybdenum oxide and 4.5% of bismuth oxide, arranged in a reaction tube. In detail, 1.1 g of dichloro-fluorotoluene (d=1.36 g/ml), 0.26 g of ammonia, 2 l of air and 1.1 g of water were passed through per minute. At the temperatures indicated, the reaction took place in the fluidized bed. The vapours leaving the reaction tube were condensed and washed with methanol and water. The solution obtained was analysed by gas chromatography for its content of dichloro-fluorotoluene and dichloro-fluorobenzonitriles.

At a reaction temperature of 520° C., the yield, based on dichloro-fluorotoluene reacted to 55% (=selectivity), was 81 to 85% of the theoretical yield (results of several reaction runs).

EXAMPLE 2

The ammoxidation of a dichloro-fluorotoluene mixture was repeated according to the details of Example 1, the reaction mixture leaving the reactor being washed with toluene and water. The toluene phase was distilled through a silver mirror column, 40 cm long, packed with glass rings (φ4 mm) after separating off the water phase. After stripping off the toluene, the mixture of the unreacted dichloro-fluorotoluenes was obtained at a top temperature of 41° C., a vacuum of 1.2 to 1.4 mbar and a reflux ratio of 1:1. The mixture of the nitriles which remained was fractionally distilled in vacuo at a reflux ratio of 10:1 through a column having an improved separatory action (about 40 theoretical plates). At 140 mbar, a 99.7% 2,4-dichloro-5-fluorobenzonitrile was obtained at a boiling point of 170.3° C. and a 99.2% 2,6-dichloro-3-fluorobenzonitrile was obtained at a boiling point of 182.2° C.

EXAMPLE 3

A liquid mixture of the composition 23.7% 2,4-dichloro-5-fluorotoluene, 11.4% 2,6-dichloro-3-fluorotoluene, 57.9% 2,4-dichloro-5-fluorobenzonitrile and 4.3% 2,6-dichloro-3-fluorobenzonitrile was seeded at room temperature with crystals of >99% 2,4-dichloro-5-fluorobenzonitrile. After a short time, plenty of sturdy crystals were formed, which proved after filtering off without further washing with a solvent to be 97% 2,4-dichloro-5-fluorobenzonitrile (GC); as an impurity they still contained 1.7% of 2,4-dichloro-5-fluorotoluene and only 0.2% of 2,6-dichloro-3-fluorobenzonitrile (remainder unidentified).

EXAMPLE 4

A gas mixture, as indicated in Example 1, was passed at 470° C. through catalyst granules having a grain diameter of 0.25 mm, consisting of a mixture of 20% vanadyl phosphate, 20% boron phosphorus oxide, 20% tin(IV) pyrophosphate and 40% $SiO_2$. The reaction gases were washed with methanol and water after leaving the reaction tube, and the solution obtained was analysed (GC). At a conversion of 70% of the dichloro-fluorotoluene mixture, a yield of 75% (=selectivity) of dichloro-fluorobenzonitrile mixture was found, based on its conversion.

What is claimed is:

1. A process for the preparation of 2,4-dichloro-5-fluorobenzonitrile and 2,6-dichloro-3-fluorobenzonitrile, in which a mixture of 2,4-dichloro-5-fluorotoluene and 2,6-dichloro-3-fluorotoluene is reacted with ammonia, air and steam in a molar ratio of dichloro-fluorotoluene:ammonia:air:steam=1:1–3:7.5–15:0–10 in the gas phase at a temperature of 350° to 550° C. on an ammoxidation catalyst to give a product mixture of said nitriles.

2. The process of to claim 1, wherein said dichloro-fluorotoluene is a mixture of 60 to 90% of 2,4-dichloro-5-fluorotoluene and 40 to 10% of 2,6-dichloro-3-fluorotoluene.

3. The process of claim 1, wherein the dichloro-fluorotoluene isomer mixture is obtained from a double nuclear chlorination of m-fluorotoluene.

4. The process of claim 1, wherein the ammoxidation is carried out in the temperature range from 400° to 530° C.

5. The process of claim 1, wherein the reaction is carried out at a molar ratio of dichloro-fluorotoluene:ammonia:air:steam of 1:1.1–1.5:7.5–15:5–10.

6. The process of claim 1, wherein the product mixture is separated by distillation.

7. The process of claim 1, wherein the product mixture is separated by crystallisation.

8. The process of claim 7, in which the 2,4-dichloro-5-fluorobenzonitrile is crystallized and the crystals are separated from the product mixture.

* * * * *

UNITED STATES PATENT AND TRADEMARK OFFICE
CERTIFICATE OF CORRECTION

PATENT NO. : 5,670,694
DATED : September 23, 1997
INVENTOR(S) : Hagedorn, et al.

It is certified that error appears in the above-indentified patent and that said Letters Patent is hereby corrected as shown below:

Col. 4, line 30    After " wherein " insert -- the --

Col. 4, line 44    Delete " wherein " and substitute -- in which --

Signed and Sealed this

Twenty-first Day of July, 1998

Attest:

Attesting Officer

BRUCE LEHMAN

Commissioner of Patents and Trademarks

UNITED STATES PATENT AND TRADEMARK OFFICE
CERTIFICATE OF CORRECTION

PATENT NO. : 5,670,694
DATED : September 23, 1997
INVENTOR(S) : Ferdinand Hagedorn, et al It is certified that error appears in the above-identified patent and that said Letters Patent is hereby corrected as shown below:

Column 4, line 30, after "wherein" insert --the--

Column 4, line 44, delete " wherein" and substitute in which--.

This certificate supersedes Certificate of Correction issued July 21, 1998.

Signed and Sealed this

Fifteenth Day of December, 1998

Attest:

BRUCE LEHMAN

*Attesting Officer*   *Commissioner of Patents and Trademarks*